United States Patent [19]
Sachse et al.

[11] Patent Number: 6,005,110
[45] Date of Patent: Dec. 21, 1999

[54] PROCESS FOR THE PRODUCTION OF ENDOTROPINE

[75] Inventors: Rolf Sachse, Berlin; Albert Schaupp, Strullendorf, both of Germany

[73] Assignee: Dr.R.Pfleger Chemische Fabrik GmbH, Bamberg, Germany

[21] Appl. No.: 09/090,637

[22] Filed: Jun. 4, 1998

[30]     Foreign Application Priority Data

Jun. 14, 1997 [EP]  European Pat. Off. .............. 97109714

[51] Int. Cl.⁶ ................................................. C07D 451/06
[52] U.S. Cl. ............................................................ 546/127
[58] Field of Search ............................................ 546/127

[56]             References Cited

U.S. PATENT DOCUMENTS

| | | | |
|---|---|---|---|
| 2,366,760 | 1/1945 | Van De Kamp et al. .............. | 546/127 |
| 2,746,976 | 5/1956 | Stoll et al. ............................... | 546/476 |

OTHER PUBLICATIONS

Chemical Abstracts, vol. 99, No. 15, Abstract 99:122721a; Kollas, Laszlo, et al "Stereoselective Reduction of Nortropinones with a Homogeneous Catalyst", Oct. 10, 1983.

Chemical Abstracts, vol. 93, No. 13, Abstract 93:132665a; Maksudov, A.M., et al "Tropine Preparation Method", Sep. 29, 1980.

Chemical Abstracts, vol. 97, No. 23, Abstract 97:198428q; Chou Ta Shue "Stereoselective Preparation of Tropine"; Dec. 6, 1982.

Chemical Abstracts, vol. 83, No. 23, Abstract 19351d; Jain, M.P., et al "Modified Process for the Synthesis of Tropine", Dec. 8, 1975.

*Primary Examiner*—Bernard Dentz
*Attorney, Agent, or Firm*—Roberts & Mercanti, L.L.P.

[57]             ABSTRACT

A process for the production of endotropine by catalytically reducing tropanone with hydrogen with Raney nickel or Raney copper. This process is conducted with tropanone in an aqueous solution absent of organic solvents, in a closed system, at atmospheric pressure and ambient temperature and subject to turbulent action at 1000 to 1500 r.p.m. The process leads to average yields of 94%. The process improves on prior art processes which use an overpressure and organic solvents which involve a high fire and explosion risk.

17 Claims, No Drawings

PROCESS FOR THE PRODUCTION OF ENDOTROPINE

BACKGROUND OF THE INVENTION

1. Field of the Invention

The invention relates to a process for the production of endotropine by the reduction of tropanone with hydrogen catalytically activated by Raney nickel or Raney copper catalyst. Tropine is also known as 3α-tropanol, 3α-hydroxytropane, 1αH, 5αH-tropan-3α-ol, and 8-methyl-8-azabicyclo-[3,2,1]-nonan-3α-ol (CAS [120-29-6]).

2. Description of the Prior Art

Endotropine is an important substance for the production of nortropine by oxidative methylation, which is in turn used for the production of important azoniaspironortropanol esters, which are used as pharmaceuticals, particularly spasmolytics (cf. German patent 1 194 42).

U.S. Pat. No. 2,366,760 describes the preparation of tropine from tropanone by catalytic reduction with hydrogen activated by a Raney nickel catalyst, without giving the yield. The reaction is performed under pressure and in an organic solvent, preferably ethanol, giving a quantitative yield. This procedure involves high apparatus expenditure with pressure vessels or autoclaves. By the use of organic solvents in conjunction with Raney nickel catalysts there is a high fire or explosion risk when working up the reaction batch. Corresponding accidents are well known from practical experience.

U.S. Pat. No. 2,746,976 describes the preparation of tropine, using an autoclave as the reaction vessel and an organic solvent, at an operating pressure of 60 atmospheres overpressure. The aforementioned disadvantages once again arise. Chemical Abstract 99 (15), 122, 721 a describes a catalytic hydrogenation of tropanone in the presence of a rhodium-phosphine complex.

Processes in which endotropine is produced by the hydrogenation of tropanone in the presence of a Raney nickel catalyst are shown in (Chemical Abstracts 97 (23), 198, 428q, Chemical Abstracts 93 (13), 132 665a and Chemical Abstracts 83 (23), 193 5611). In the first-mentioned literature reference, a yield of 92% is given. Thus, the hitherto known processes only make it possible to produce tropine in the presence of organic solvents and when using a high pressure.

It has now been surprisingly found that it is possible to reduce tropanone selectively and with good yields without using a high pressure and without using organic solvents so as to give tropine when an aqueous mixture of tropanone is reduced by hydrogen when subjected to turbulent action at atmospheric pressure and ambient temperatures at 1000 to 1500 r.p.m. It could not be foreseen on the basis of the hitherto known processes that this reaction would take place smoothly and also stereoselectively supplies the desired endotropine compound.

SUMMARY OF THE INVENTION

The invention provides a process for the production of endotropine which comprises the reduction of tropanone with hydrogen, catalytically activated by Raney nickel or Raney copper, wherein the tropanone, in aqueous solution with hydrogen, in a closed system, at atmospheric pressure and ambient temperature is subject to turbulent action at 1000 to 1500 r.p.m.

The invention also provides a process for the production of endotropine which comprises catalytically reducing a tropanone containing suspension with hydrogen in the presence of a Raney nickel or Raney copper catalyst under turbulent conditions.

The invention further provides a process for the production of endotropine which comprises catalytically reducing an aqueous suspension of tropanone absent of organic solvents, with hydrogen in the presence of a Raney nickel or Raney copper catalyst, in a closed system, under turbulent conditions, at about atmospheric pressure, at a temperature of about 15° C. to about 25° C. and under turbulent stirring at about 1000 to about 1500 r.p.m.

DETAILED DESCRIPTION OF THE PREFERRED EMBODIMENT

In the practice of the invention, endotropine, is produced by catalytically reducing tropanone with hydrogen in the presence of catalytic amount of a Raney nickel or Raney copper catalyst. Preferably the tropanone is reacted in the form of an aqueous suspension absent of any organic solvents. In the preferred embodiment, the tropanone is present in the aqueous suspension in an amount of from about 10% to about 20%, more preferably about 10% by weight of the suspension. Preferably the Raney nickel or Raney copper catalyst is present in a catalytic amount ranging from about 5% to about 15% by weight of the tropanone in the suspension. The reduction process is preferably conducted in a closed system wherein an excess of hydrogen gas introduced into the suspension. Preferably the reaction is conducted at about atmospheric pressure or below and more preferably at about atmospheric pressure. Preferably the reduction is conducted at about ambient temperatures and preferably at a temperature of about 15° C. to about 25° C. After introduction of hydrogen, the reaction mass is subjected to turbulent stirring at about 1000 to about 1500 r.p.m. until essentially no more hydrogen is taken up. The reaction mass is then subjected to isolation such as by filtering, mixing with aqueous sodium hydroxide, extraction with dichloromethane and crystallization.

EXAMPLE 1

14 g of tropinone are dissolved with stirring in 100 ml of an aqueous suspension of Raney nickel catalyst, having an approximately 10% solids fraction. The complete mixture in a closed system is then subject to turbulent action in a hydrogen atmosphere, at atmospheric pressure, at ambient temperature with stirring at approximately 1300 r.p.m., until the taking up of hydrogen is ended.

The tropinone is then substantially completely reacted and a gas chromatogram shows at least 98% by area tropine and a maximum of 2% by area pseudotropine. The catalyst is separated by filtration and the clear, aqueous filtrate is mixed portionwise with 14 g of sodium hydroxide and then extracted with three 20 ml dichloromethane portions. The extracts are combined and concentrated. 13.5 g of a colorless, thick oil are left behind as residue and completely crystallize after standing briefly. The white crystals melt at approximately 60° C. The process yields 94% of endotropine.

EXAMPLE 2

Example 1 is repeated except Raney copper is used instead of Raney nickel. Similar results are observed.

What is claimed is:

1. A process for the production of endotropine which comprises the reduction of tropanone with hydrogen, catalytically activated by Raney nickel or Raney copper, wherein the tropanone, in aqueous solution with hydrogen, in a closed system, at atmospheric pressure and ambient temperature is subject to turbulent action at 1000 to 1500 r.p.m.

2. A process according to claim 1, wherein the turbulent action takes place at about 1300 r.p.m.

3. The process of claim 1 which is conducted by use of a high-speed stirrer.

4. The process of claim 2 which is conducted by use of a high-speed stirrer.

5. A process for the production of endotropine which comprises catalytically reducing a tropanone containing suspension with hydrogen in the presence of a Raney nickel or Raney copper catalyst under turbulent conditions, wherein the tropanone is in an aqueous suspension.

6. The process of claim 5 which is conducted in the absence of organic solvents.

7. The process of claim 5 which is conducted at about atmospheric pressure or below.

8. The process of claim 5 which is conducted at about atmospheric pressure.

9. The process of claim 5 which is conducted at a temperature of about 15° C. to about 25° C.

10. The process of claim 5 which is conducted in a closed system.

11. The process of claim 5 which is conducted by turbulent stirring at about 1000 to about 1500 r.p.m.

12. The process of claim 5 which is conducted with Raney nickel.

13. The process of claim 5 which is conducted with Raney copper.

14. The process of claim 5 wherein the tropanone is in an aqueous suspension absent of organic solvents, which is conducted in a closed system, at about atmospheric pressure, at a temperature of about 15° C. to about 25° C. and by turbulent stirring at about 1000 to about 1500 r.p.m.

15. The process of claim 5 which is conducted with Raney nickel.

16. The process of claim 5 which is conducted with Raney copper.

17. A process for the production of endotropine which comprises catalytically reducing an aqueous suspension of tropanone absent of organic solvents, with hydrogen in the presence of a Raney nickel or Raney copper catalyst, in a closed system, under turbulent conditions, at about atmospheric pressure, at a temperature of about 15° C. to about 25° C. and under turbulent stirring at about 1000 to about 1500 r.p.m.

* * * * *